United States Patent [19]

Blanco et al.

[11] Patent Number: 5,224,585
[45] Date of Patent: Jul. 6, 1993

[54] CARRIER FOR CODED CONTAINERS

[75] Inventors: Ernesto E. Blanco, Belmont; James W. Winkleman, Brookline; Donald R. Wybenga, Hull; Catherine J. Anderson, Cambridge, all of Mass.; Kenneth A. Pasch, Chicago, Ill.; Robert E. Lopez, Natick; Anne M. Schreiter, Bradford, both of Mass.

[73] Assignee: Brigham & Women's Hospital, Boston, Mass.

[21] Appl. No.: 867,176

[22] Filed: Apr. 10, 1992

[51] Int. Cl.⁵ .............................................. B65G 37/00
[52] U.S. Cl. ............................ 198/803.01; 198/690.1
[58] Field of Search ............ 198/803.01, 465.1, 690.1; 209/583, 569, 912, 931; 235/475, 479, 486

[56] References Cited

U.S. PATENT DOCUMENTS

| | | |
|---|---|---|
| 2,103,681 | 9/1936 | Klaucke . |
| 3,090,478 | 8/1960 | Stanley . |
| 3,854,889 | 12/1974 | Lemelson ...................... 198/465.1 X |
| 3,941,237 | 3/1976 | MacGregor, Jr. . |
| 4,159,762 | 7/1979 | Bulwith .......................... 198/803.01 |
| 4,356,909 | 11/1982 | November et al. ............. 198/465.2 |
| 4,454,939 | 6/1984 | Kampf et al. ................ 198/465.2 X |
| 4,595,562 | 6/1986 | Liston et al. . |
| 4,958,716 | 9/1990 | Matsuo et al. ................ 198/465.1 X |
| 5,014,868 | 5/1991 | Wittig et al. . |
| 5,150,795 | 9/1992 | Nakayama et al. ............. 209/569 X |

FOREIGN PATENT DOCUMENTS

| | | | |
|---|---|---|---|
| 0157112 | 7/1987 | Japan ................................. 198/690.1 |
| 0161614 | 7/1987 | Japan ................................. 198/690.1 |
| 0658049 | 4/1979 | U.S.S.R. ......................... 198/803.01 |

Primary Examiner—D. Glenn Dayoan
Attorney, Agent, or Firm—Hamilton, Brook, Smith & Reynolds

[57] ABSTRACT

A carrier for supporting a coded container in a predetermined orientation on a magnetic conveyor system having magnetic means on the carrier with at least one window in the carrier to expose a coded container held therein.

19 Claims, 5 Drawing Sheets

CARRIER FOR CODED CONTAINERS

FIELD OF THE INVENTION

This invention relates generally to conveyors and, more specifically, to carriers for supporting coded containers in predetermined orientation on a magnetic conveyor.

BACKGROUND OF THE INVENTION

Modern medical laboratories perform various analytical tests on specimens of the same type and on specimens of different types and at numerous workstations, often in the same room or in adjoining rooms. The specimens are presented to the laboratory in containers of various sizes, shapes and colors, with coverings or caps, etc. For example, in one large hospital, thirty-two containers are employed routinely. This is obviously a complex operation. For example, different types of urinalysis testing as well as blood testing may be performed. The blood may be received either with or without anticoagulants, depending on the analyte to be tested and the method of testing. The system is further complicated by the fact that the specimens come from numerous patients. This requires absolute accuracy in specimen identification and traffic control. It is in this general environment that the present invention is intended to perform.

It is an object of this invention to automate the preanalytical portions of such a laboratory by the use of a computer operated magnetic conveyor system.

Magnetic conveyors basically fall into two broad categories. The first employs magnets fixed to traveling nonmagnetic belts such as rubber or neoprene. The magnets are releasably engageable with ferromagnetic articles or articles having at least a ferromagnetic portion. While traveling on the conveyor, the articles are maintained in fixed position in engagement with their respective magnets on the belt and do not slide or otherwise move relative to the conveyor belt.

The second category of magnetic conveyors includes those in which the conveyed articles, themselves, either are magnetic or have magnetic means on them. They are carried by ferromagnetic belts as, for example, stainless steel. Once positioned on the traveling belt, the conveyed articles do not always stay in their original locations. Since the entire belt is ferromagnetic, the conveyed articles may slide relative to the belt while still maintaining their magnetic attraction. An advantage of this type of system is that should there be a stoppage of one article, the other articles may pile up against it without doing damage because, while the articles themselves may come to a halt, the traveling belt can continue moving beneath them. This type of conveyor is ideally suited for automating a medical laboratory.

In instances where a conveyor system is intended to convey articles that are not homogeneous or destined for the same ultimate locations, as in medical laboratories, the conveyor system must, of necessity, have more than one conveyor segment, be branched or have multilevels with traffic control means to direct the nonhomogeneous articles to their destinations in accordance with their kind, shape, color, contents, etc. The basic design of such modules should ideally allow for asynchronous movement along connected segments.

SUMMARY OF THE INVENTION

The invention resides in a carrier for supporting a coded container in a predetermined orientation on a magnetic conveyor system of the type having a ferromagnetic continuous belt. The carrier comprises an open top receptacle. There are magnetic means on the receptacle for engagement with traveling ferromagnetic belts. The belts may move horizontally or vertically or at varying angles with the horizontal. Window means are located at the front of the receptacle and there are means in the receptacle to orient the coded container such that the code is visible through the window. There are also means in the receptacle to position the container releasably in engagement with the orienting means. The positioning means are flexable and yieldable to accommodate coded containers of varying sizes and shapes.

The magnetic means are located both on the bottom of the receptacle and on at least one side of the receptacle. Magnetic means located on the bottom are engageable with belts which move substantially horizontally and the magnetic means on the side of the receptacle are engageable with traveling ferromagnetic belts which move in substantially vertical directions either up or down.

In a preferred embodiment, the window means comprises a vertical slit in the front of the receptacle.

In a further embodiment, the window means may be a transparent side of the receptacle or the entire receptacle may be made transparent or one side may be open.

In another embodiment, the entire receptacle may be clear plastic or the window means may include two transparent sides such as clear plastic or vertical slits on two facing sides such as the front and back of the receptacle.

In a preferred embodiment of the invention, the orienting means comprises interior walls in the container converging toward the slit to locate the container in front of the slit so the code is visible through the slit. The positioning means is one or more springs urging or biasing the container into engagement with the converging walls to place the coded container close to the slit.

Whereas the container may be of any cross-sectional shape, the preferred form is rectangular.

The above and other features of the invention including various and novel details of construction and combinations of parts will now be more particularly described with reference to the accompanying drawings and pointed out in the claims. It will be understood that the particular carrier for a coded container embodying the invention is shown by way of illustration only and not as a limitation of the invention. The principles and features of this invention may be employed in varied and numerous embodiments without departing from the scope of the invention.

DETAILED DESCRIPTION

Figure 1:
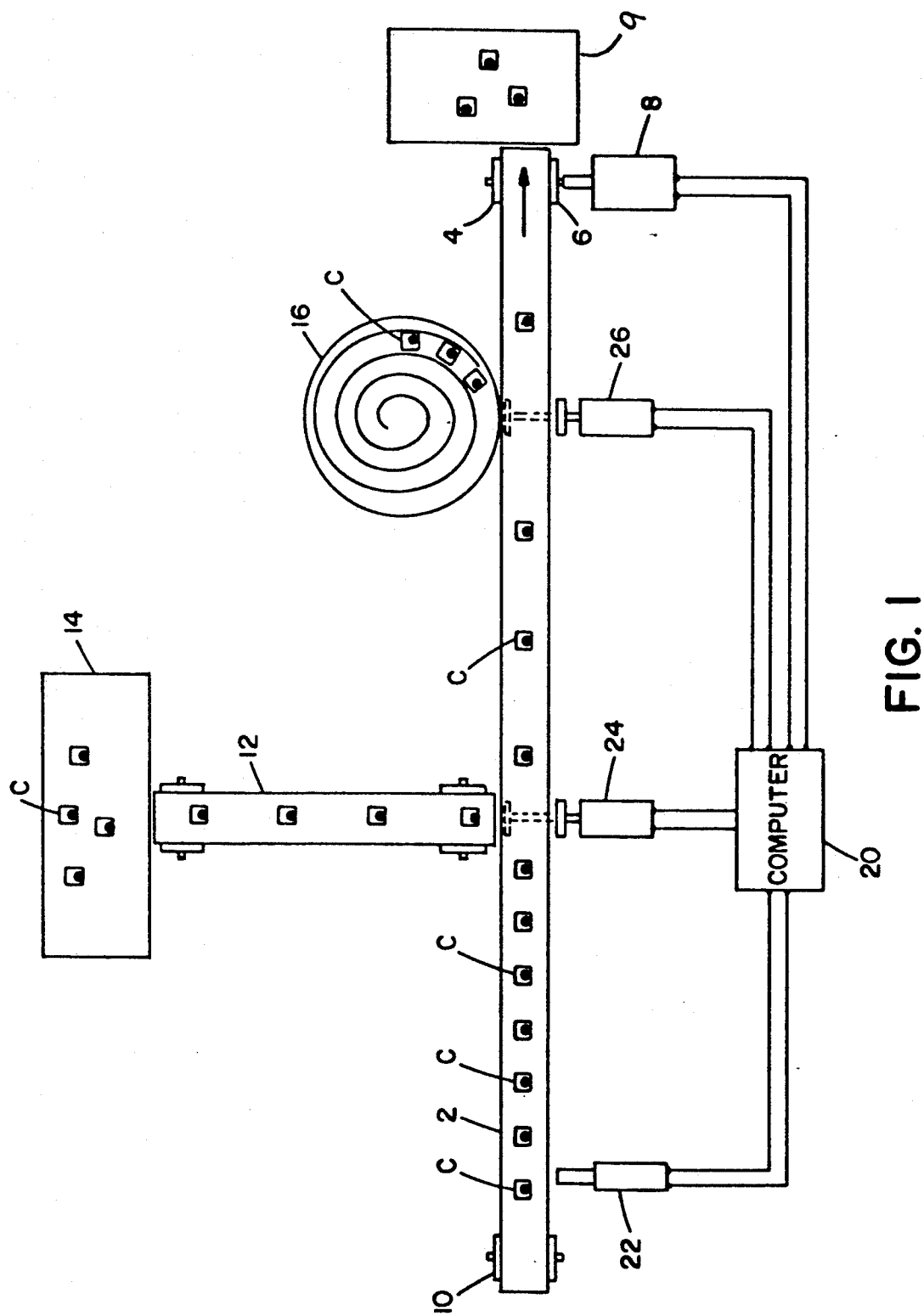
FIG. 1 is a schematic plan view of a conveyor system for moving receptacles containing coded containers to a plurality of stations.

FIG. 1 is a schematic plan view of a magnetic conveyor system embodying the invention. It includes a first continuous conveyor belt 2 of ferromagnetic material such as ferridic stainless steel or plated carbon steel. It passes around and is driven by an pulley 6 driven by an electric motor 6 in the direction of the arrow above the motor. If desired, the pulley 6 may have a rubber or other elastomeric driving surface. A collection area 9 is located at the end of the belt 2. The opposite end of the belt passes around an idler pulley 10. A second ferromagnetic belt 12 is located at right angles to the first belt and leads to a work station 14. A helical accumulator 16 is located adjacent the belt 2. The entire system is controlled by a master computer 20.

It will be understood that the particular conveyor system illustrated in FIG. 1 is shown for illustrative purposes only, and many other components may be added along with additional conveyor belts as needed for the particular installation.

Located adjacent the computer is a code reader 22 and, for purposes of this invention, will be considered to be a bar code reader. The reader is connected to the computer into which it feeds data. Also connected to the computer is a pusher or ejector mechanism 24 opposite the second belt 12. A second ejector mechanism 26 is also connected and triggered by computer 20 and is located opposite the accumulator 16.

A plurality of carriers, generally designated C are supported on and moved by the conveyor belts from left to right, as viewed in FIG. 1. Each carrier comprises an open top receptacle carrying within it a coded container such as a vial supplied with a bar code identifying the patient, the contents of the vial, the test to be performed and other pertinent information. The containers may be of varying sizes.

The receptacle may have a colored tag as long as it is either removable to gain access to the interior of the receptacle or have at least one open side for the same purpose.

The code reader 22 reads the information on the coded label and supplies it to the computer 20. When a given carrier has its label read, the computer compares the information with prestored data and, if the contents of the coded container are to be analyzed at work station 14, when the carrier reaches the second or transverse belt 12, the computer will activate the ejector 24 to push the carrier C with its vial onto the belt 12 to be delivered to the work station 14.

When another carrier passes the reader 22, its label may call for a different test, and when this information is fed to the computer, the computer will not signal the ejector to move the receptacle from the first belt 2, but rather let it continue on the belt until it reaches, for example, the helical accumulator 16. Thereupon the computer signals the ejector 26 to move from the solid line to the dotted line position, thereby sliding the receptacle across the belt 2 into the accumulator 16 where it will join other receptacles carrying vials with specimens to be subjected to the same test.

Figure 2:
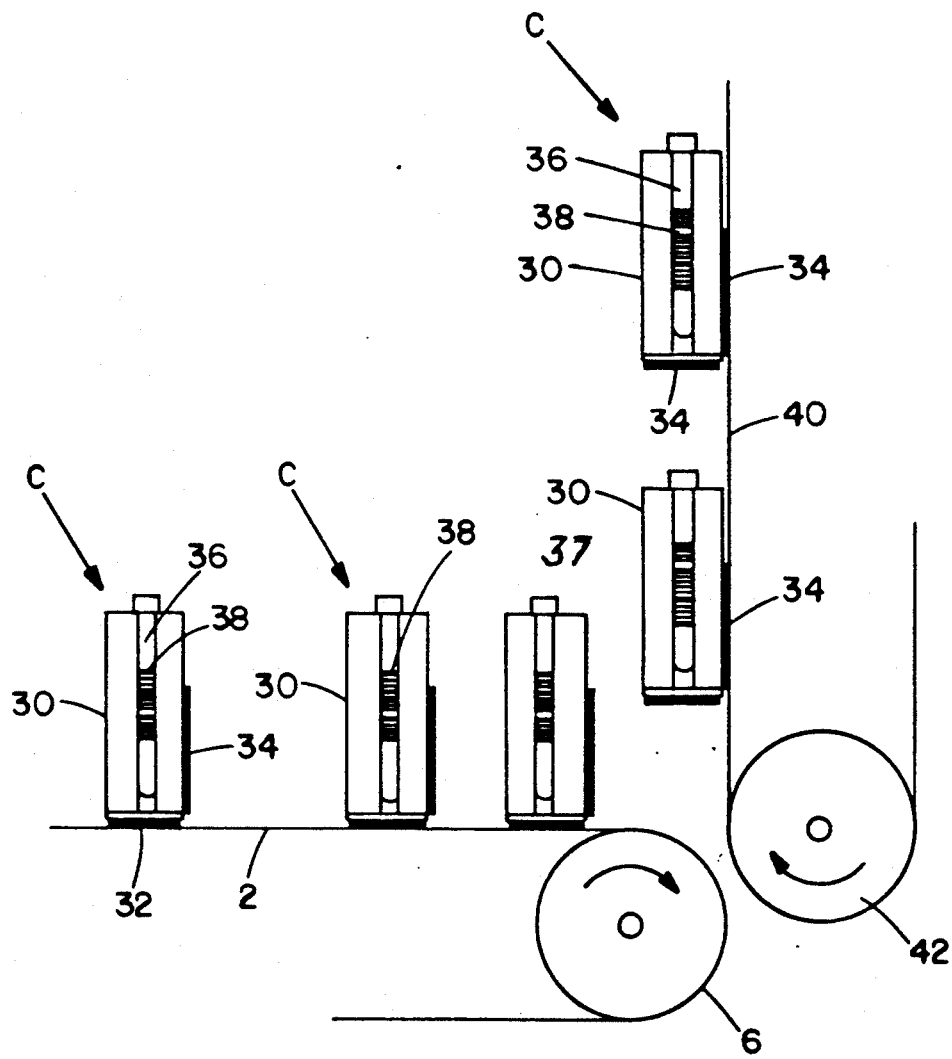
FIG. 2 is a schematic side view of a portion of the conveyor system.

Whereas FIG. 1 shows a conveyor system operating only in a horizontal plane, FIG. 2 shows the system having belt segments operating both horizontally and vertically to convey the receptacles or carriers C to a higher level as, for example, to pass over an aisle of the laboratory. Conveyor belt 2 is shown supporting a plurality of carriers C in the form of an open top receptacle 30. Each receptacle has first magnetic means 32 on its bottom and second magnetic means 34 on one of its sides. They are flat magnets located 90° from each other. The magnet 34 is employed when the carrier is moved upwardly or downwardly by a vertical conveyor belt. The magnet 32 is employed for horizontal movement.

Within the receptacles are stoppered containers herein illustrated as vials 36 with stoppers 37. Each container has a coded label 38 secured to it. The code is illustrated as a bar code, but it could be any machine readable code such as numeric characters. The color of the stopper may be used to identify the contents of the vial. As an alternative, the vials themselves may be color coded to indicate their contents or need for speed in testing. A second conveyor segment including a ferromagnetic belt 40, driven by an elastomeric pulley 42, is located adjacent the end of the first belt 2. As each receptacle 30 reaches the end of the belt 2, its magnet 34 engages the belt 40 and it is lifted upwardly by the belt.

Figure 4:
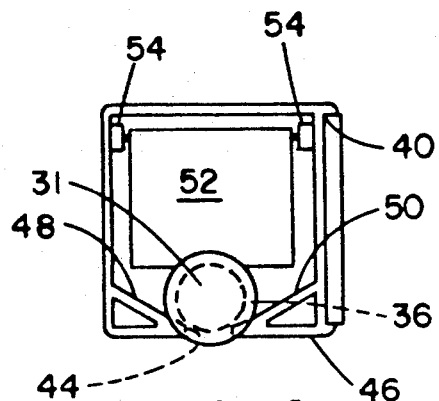
FIG. 4 is a top view of the receptacle.
Figure 3:
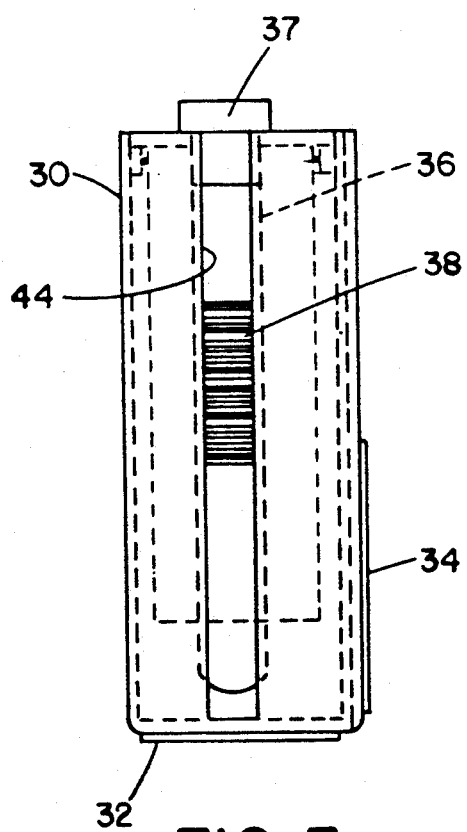
FIG. 3 is a front view of the receptacle.
Figure 5:
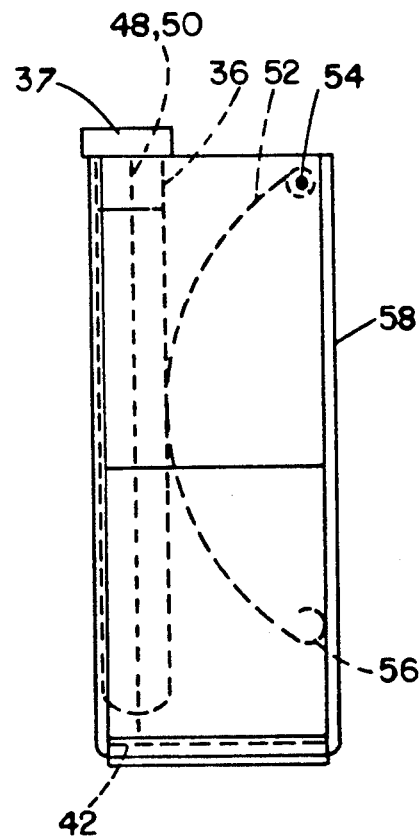
FIG. 5 is a side view of the receptacle.

The carriers 30 will be seen in greater detail in FIGS. 3 to 5. The carrier per se is a molded plastic, receptacle having a recess 40 on one side into which the magnetic 34 is fitted. It has a recess 42 in the bottom into which magnet 32 is fitted. A window in the form of a vertical slit 44 runs from top to bottom of the front wall 46 of the receptacle.

Means for orienting the coded container 36 so that its code 38 is visible through the window comprises interior walls 48 and 50 which converge toward the slit 44.

Spring means are located in the receptacle to bias or urge the container releasably into engagement with the converging interior walls 48 and 50. The spring means in the illustrative example comprises a single leaf spring 52 which is pivotally mounted on gibbs 54 at the top of inside of the rear wall of the receptacle. As will best be seen in FIG. 5, the spring 52 is curvilinear and bears directly on the container or vial 36 urging it forwardly to the window or slit 44. Coil springs or springy air bladders may also be used.

With this construction, it is possible to accommodate containers of various diameters with the spring 52 maintaining engagement with the containers and its lower end 56 sliding up or down on the interior of the rear wall 58 of the receptacle depending on the side of the container in the carrier. To remove the container or vial 36 at its destination, it is merely pulled upwardly out of the receptacle 30.

The bottom magnet 32 is initially placed on the horizontal belt 2 and, through engagement with various horizontal and/or vertical belts, the container with its specimen ultimately reaches its destination completely under the control of the computer 20 and one or more code readers 22.

Figure 7:
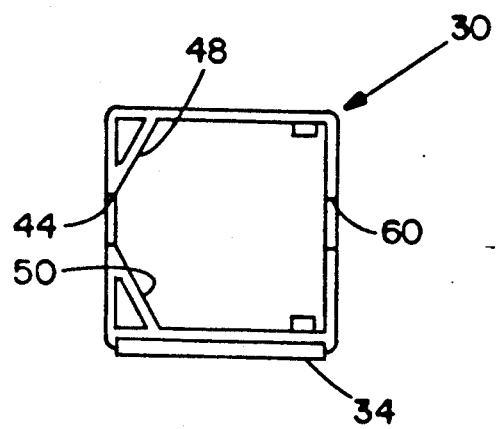
FIG. 7 is a top view of the second embodiment of the receptacle.
Figure 6:
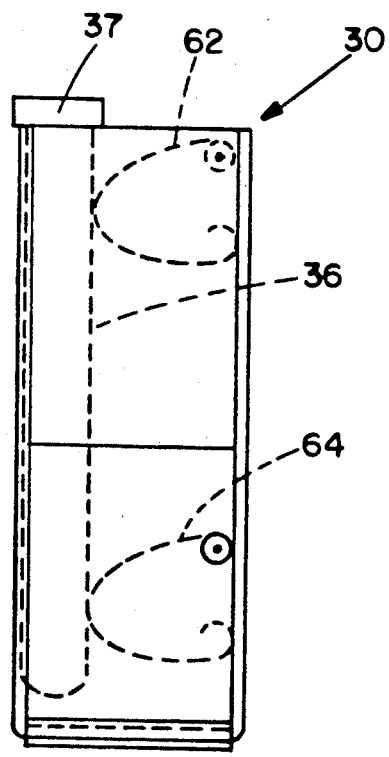
FIG. 6 is a side view of a second embodiment of the receptacle.

An alternative construction of the receptacle 30 is seen in FIGS. 6 and 7. A second slit or window 60 is positioned in the rear wall of the receptacle 30 to assure that the bar code or other coded label will be visible should the technician initially insert the code out of alignment with the front window 44. In this case, additional readers would be positioned at strategic places along the system to read the back of the carriers as well as the reader 22 which reads the front side. In this case, with the additional slit or window 60 in the rear of the carrier, the spring 52 would normally block the reader's view of the coded vial. However, a pair of springs 62 and 64 would be employed above and below the center of the vial where the label normally would be placed.

Figure 8:
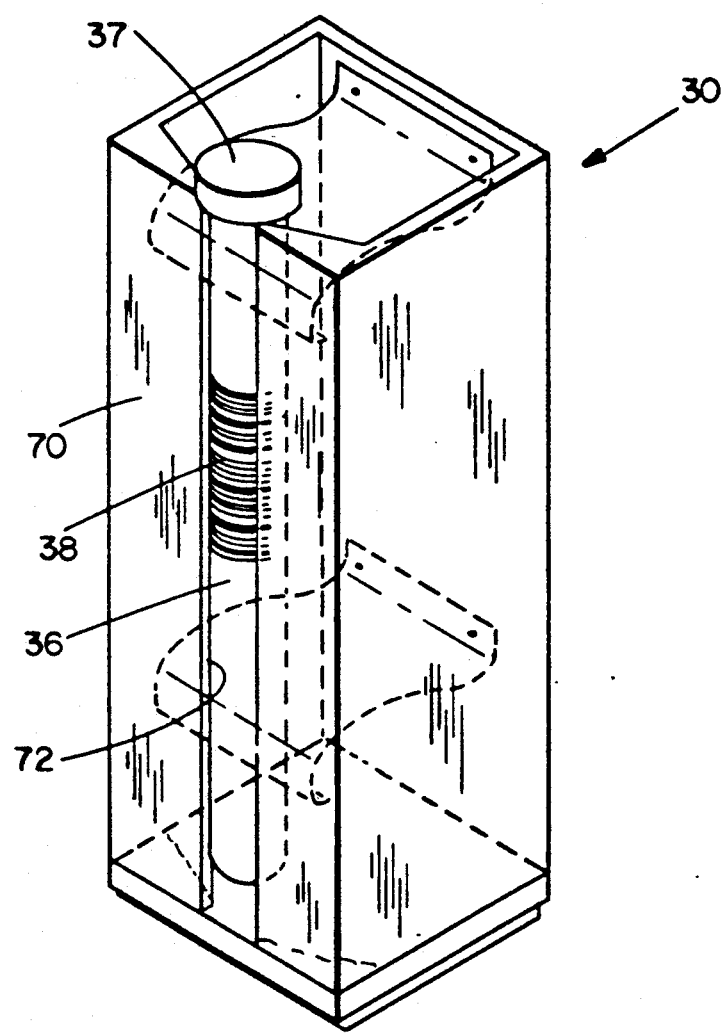
FIG. 8 is a perspective view another embodiment of the receptacle.

Other embodiments of the invention will be seen in FIG. 8. The entire carrier may be made of a transparent plastic to make the coded label 38 visible in all directions and to more readily let a technician know if a carrier is in the system without its coded container in it. Alternately, only the front wall may be transparent, with or without a slot 72.

We claim:

1. A carrier for supporting a coded container in a predetermined orientation on a magnetic conveyor system, the carrier comprising:
    a receptacle having at least one opening leading to a substantially rectangular interior larger than the size of the coded container intended to be supported by the carrier;
    magnetic means on the receptacle;
    a window in the front of the receptacle;
    means to locate the coded container in the receptacle in front of the window so the code is visible through the window when the container is inserted into the carrier with the code facing the window; and
    means in the receptacle to urge the container releasably into engagement with the locating means.

2. A carrier for supporting a coded container in a predetermined orientation on a magnetic conveyor system, the carrier comprising:
    a receptacle having at least one opening and a substantially rectangular interior larger than the size of the coded container intended to be supported by the carrier;
    magnetic means on the bottom of the receptacle;
    magnetic means on one side of the receptacle;
    a window in the front of the receptacle;
    means contiguous to the window to locate the coded container in the receptacle in front of the window so the code is visible through the window when the container is inserted into the carrier with the code facing the window; and
    biasing means in the receptacle to urge the container releasably into engagement with the locating means.

3. A carrier for supporting a coded container in a predetermined orientation on a magnetic conveyor system, the carrier comprising:
    a receptacle having at least one opening;
    magnetic means on the bottom of the receptacle;
    a vertical slit in the front of the receptacle;
    interior walls converging toward the slit to locate the container in front of the slit so the code is visible through the slit when the container is inserted into the carrier with the code facing the window; and
    spring means in the receptacle to urge the container releasably into engagement with the converging interior walls.

4. A carrier as in claim 1 wherein there is a second window opposite the first mentioned window.

5. A carrier as in claim 2 wherein there is a second window opposite the first mentioned window.

6. A carrier as in claim 3 wherein there is a second slit opposite the first mentioned slit.

7. A carrier as in claim 1 wherein the magnetic means comprises two flat magnets oriented 90° from each other.

8. A carrier as in claim 2 wherein the magnetic means are flat and oriented 90° from each other.

9. A carrier as in claim 3 wherein the magnetic means are flat and oriented 90° from each other.

10. A carrier according to claim 1 wherein the receptacle is transparent.

11. A carrier according to claim 1 wherein the window is a transparent side of the receptacle.

12. A carrier according to claim 2 wherein the window is a transparent side of the receptacle.

13. A carrier as in claim 1 wherein the receptacle is rectangular in cross section.

14. A carrier as in claim 2 wherein the receptacle is rectangular in cross section.

15. A carrier as in claim 3 wherein the receptacle is rectangular in cross section.

16. A carrier according to claim 1 wherein the positioning means is a spring.

17. A carrier according to claim 2 wherein the biasing means is a spring.

18. A carrier according to claim 3 wherein the spring means is a single leaf spring.

19. A carrier according to claim 3 wherein the spring means is a plurality of springs.

* * * * *

UNITED STATES PATENT AND TRADEMARK OFFICE
CERTIFICATE OF CORRECTION

PATENT NO. : 5,224,585

DATED : July 6, 1993

INVENTOR(S) : Ernesto E. Blanco, et al.

It is certified that error appears in the above-identified patent and that said Letters Patent is hereby corrected as shown below:

Column 6, line 8:

Claim 3, line 6 has been omitted. Please insert --magnetic means on one side of the receptacle;--.

Signed and Sealed this

Twenty-second Day of February, 1994

Attest:

BRUCE LEHMAN

Attesting Officer    Commissioner of Patents and Trademarks